(12) United States Patent
Chodkowski et al.

(10) Patent No.: US 10,518,053 B2
(45) Date of Patent: Dec. 31, 2019

(54) SUBNASAL SEALING CUSHION AND PATIENT INTERFACE DEVICE EMPLOYING SAME

(71) Applicant: KONINKLIJKE PHILIPS N.V., Eindhoven (NL)

(72) Inventors: Lauren Patricia Chodkowski, Pittsburgh, PA (US); Richard Thomas Haibach, Verona, PA (US)

(73) Assignee: Koninklijke Philips N.V., Eindhoven (NL)

( * ) Notice: Subject to any disclaimer, the term of this patent is extended or adjusted under 35 U.S.C. 154(b) by 731 days.

(21) Appl. No.: 14/772,492

(22) PCT Filed: Mar. 10, 2014

(86) PCT No.: PCT/IB2014/059573
§ 371 (c)(1),
(2) Date: Sep. 3, 2015

(87) PCT Pub. No.: WO2014/141029
PCT Pub. Date: Sep. 18, 2014

(65) Prior Publication Data
US 2016/0022944 A1 Jan. 28, 2016

Related U.S. Application Data

(60) Provisional application No. 61/779,153, filed on Mar. 13, 2013.

(51) Int. Cl.
*A61M 16/06* (2006.01)

(52) U.S. Cl.
CPC .... *A61M 16/0616* (2014.02); *A61M 16/0622* (2014.02); *A61M 2016/0661* (2013.01); *A61M 2210/0618* (2013.01)

(58) Field of Classification Search
CPC .......... A61M 16/0616; A61M 16/0622; A61M 2016/0661; A61M 2210/0618
(Continued)

(56) References Cited

U.S. PATENT DOCUMENTS

| 6,012,455 A | 1/2000 | Goldstein |
| 8,371,302 B2 * | 2/2013 | Ging ..................... A61M 16/06 128/206.24 |

(Continued)

FOREIGN PATENT DOCUMENTS

| EP | 2388039 A1 | 11/2011 |
| GB | 2385533 A | 8/2003 |

(Continued)

*Primary Examiner* — Andrew S Lo
(74) *Attorney, Agent, or Firm* — Michael W. Haas

(57) ABSTRACT

A subnasal sealing cushion for a patient interface device includes a cushion member having a front side and a rear side, the rear side being structured to face a face of the user responsive to the patient interface device being donned, the cushion member including: a support portion having an outer wall and a support structure coupled to the outer wall and extending longitudinally along a first direction extending from the front side to the rear side, and a sealing flap portion coupled a nasal shelf portion, the nasal shelf portion defining a nasal orifice and being structured to contact a bottom of a nose of the user to create a seal therewith responsive to the patient interface device being donned by the user, wherein the support structure is positioned under and spaced from a bottom of the nasal shelf portion.

16 Claims, 14 Drawing Sheets

(58) Field of Classification Search
USPC .................................................. 128/206.24
See application file for complete search history.

(56) References Cited

U.S. PATENT DOCUMENTS

| | | |
|---|---|---|
| 2003/0019495 A1 | 1/2003 | Palkon |
| 2005/0199241 A1* | 9/2005 | Ging ..................... A61M 16/06 128/207.11 |
| 2007/0125385 A1* | 6/2007 | Ho ........................ A61M 16/06 128/206.26 |
| 2008/0006277 A1* | 1/2008 | Worboys ............... A61M 16/06 128/207.13 |
| 2008/0121235 A1* | 5/2008 | Ging ..................... A61M 16/06 128/207.13 |
| 2008/0230068 A1 | 9/2008 | Rudolph |
| 2009/0223522 A1 | 9/2009 | Hernandez |
| 2009/0277452 A1* | 11/2009 | Lubke ................... A61M 16/06 128/206.21 |
| 2010/0229869 A1* | 9/2010 | Ging ..................... A61M 16/06 128/205.25 |
| 2010/0319700 A1 | 12/2010 | Ng |
| 2011/0000492 A1* | 1/2011 | Veliss ............... A61M 16/0666 128/207.13 |
| 2011/0265791 A1* | 11/2011 | Ging ..................... A61M 16/06 128/202.27 |
| 2012/0012114 A1* | 1/2012 | Chandran ............. A61M 16/06 128/206.28 |
| 2012/0017912 A1* | 1/2012 | Ging ..................... A61M 16/06 128/207.11 |
| 2012/0067349 A1 | 3/2012 | Barlow |
| 2012/0145158 A1* | 6/2012 | Lubke ................... A61M 16/06 128/206.21 |
| 2013/0133658 A1* | 5/2013 | Ng ........................ A61M 16/06 128/205.24 |
| 2013/0133660 A1* | 5/2013 | Ng ........................ A61M 16/06 128/205.25 |
| 2013/0174839 A1* | 7/2013 | Ging ..................... A61M 16/06 128/202.27 |
| 2013/0199537 A1* | 8/2013 | Formica ................ A61M 16/06 128/205.25 |
| 2013/0213400 A1* | 8/2013 | Barlow ................. A61M 16/06 128/205.25 |
| 2013/0291870 A1* | 11/2013 | Ging ..................... A61M 16/06 128/205.25 |
| 2014/0202463 A1* | 7/2014 | Ging ..................... A61M 16/06 128/205.25 |
| 2014/0311493 A1* | 10/2014 | Chandran ............. A61M 16/06 128/205.25 |
| 2014/0338664 A1* | 11/2014 | Ging ..................... A61M 16/06 128/202.27 |
| 2015/0190602 A1* | 7/2015 | Barlow ................. A61M 16/06 128/206.24 |
| 2015/0196726 A1* | 7/2015 | Skipper ................ A61M 16/06 128/202.27 |

FOREIGN PATENT DOCUMENTS

| | | | |
|---|---|---|---|
| WO | WO2007133332 | * | 11/2007 |
| WO | WO2012040791 A1 | | 4/2012 |

* cited by examiner

SUBNASAL SEALING CUSHION AND PATIENT INTERFACE DEVICE EMPLOYING SAME

CROSS-REFERENCE TO RELATED APPLICATIONS

This patent application claims the priority benefit under 35 U.S.C. § 371 of international patent application no. PCT/IB2014/059573, filed Mar. 10, 2014, which claims the priority benefit under 35 U.S.C. § 119(e) of U.S. Provisional Application No. 61/779,153 filed on Mar. 13, 2013, the contents of which are herein incorporated by reference.

BACKGROUND OF THE INVENTION

1. Field of the Invention

The present invention pertains to patient interface devices structured to deliver a flow of breathing gas to a user, and, in particular, to a subnasal sealing cushion for a patient interface device that has support feature located beneath the sealing flap portion thereof 2. Description of the Related Art There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint the patient's airway open, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of the patient. The mask component may be, without limitation, a nasal/oral mask that covers the patient's nose and mouth, a nasal mask that covers the patient's nose, a nasal cushion that rests beneath the patient's nose (such as a "pillows" style nasal cushion having nasal prongs that are received within the patient's nares or a "cradle" style nasal cushion that rests beneath and covers the patient's nares), or a full face mask that covers the patient's face. Such patient interface devices may also employ other patient contacting components, such as forehead supports, cheek pads and chin pads.

The sealing cushion typically has a support portion coupled to a sealing flap portion, which may integrated together as a single part or that may be separate components that when combined together in the final assembly provide the sealing and support functions. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

One particular type of sealing cushion used non-invasive ventilation and positive pressure support therapy is what is commonly known as an inflatable subnasal sealing cushion (sometimes also called an inflated subnasal auto-seal). An inflatable subnasal sealing cushion utilizes the therapy pressure to bring the sealing surface (typically in the form of a thin sealing flap) under and around the patient's nose. More specifically, this type of sealing cushion is secured under the nose and inflates to fit around the pronasale from left alare base to right alare base. The inflation around the nose compensates for varying subnasal geometries (varying nares, alares, and/or pronasale regions). Currently, the concept utilizes very little support structure for the seal itself, but requires an anchored platform from which to inflate. However, if significant force is applied directly to the sealing side of the sealing flap, the sealing element will often drastically deform and/or collapse, thereby rendering the mask useless. In addition, the prominent crease located along the subnasal sealing path between the alare and alare base makes sealing off this area very difficult, thereby causing current inflatable subnasal sealing cushions to be prone to leaking.

SUMMARY OF THE INVENTION

Accordingly, it is an object of the present invention to provide a subnasal sealing cushion for a patient interface device that overcomes the shortcomings of conventional subnasal sealing cushions. This object is achieved according to the present invention by providing a subnasal sealing cushion that includes a support feature located beneath the sealing flap portion thereof.

In one embodiment, a subnasal sealing cushion for a patient interface device structured to deliver a flow of breathing gas to an airway of a user is provided. The subnasal sealing cushion includes a cushion member having a front side and a rear side opposite the front side, the rear side being structured to face a face of the user responsive to the patient interface device being donned by the user, the cushion member including: a support portion having an outer wall and a support structure coupled to the outer wall and extending longitudinally along a first direction, the first direction extending from the front side to the rear side, and a sealing flap portion coupled to the support portion, the sealing flap portion including a nasal shelf portion, the nasal shelf portion defining a nasal orifice and being structured to contact a bottom of a nose of the user to create a seal therewith responsive to the patient interface device being donned by the user, wherein the support structure is positioned under and spaced from a bottom of the nasal shelf portion.

In another embodiment, a subnasal sealing cushion for a patient interface device structured to deliver a flow of breathing gas to an airway of a user is provided. The subnasal sealing cushion includes a cushion member having a front side and a rear side opposite the front side, the rear side being structured to face a face of the user responsive to the patient interface device being donned by the user, the cushion member including: a support portion having a lower oral support portion, an upper nasal support portion, a support structure coupled to an outer wall of the support portion and extending longitudinally along a first direction, the first direction extending from the front side to the rear side, and a sealing flap portion coupled to the support portion, the sealing flap portion including an oral sealing portion that transitions into a nasal shelf portion, the nasal shelf portion defining a nasal orifice and being structured to contact a bottom of a nose of the user to create a seal therewith responsive to the patient interface device being donned by the user, oral sealing portion having an oral orifice that is structured to receive a mouth of the user responsive to the patient interface device being donned by the user, wherein the support structure is positioned under and spaced from a bottom of the nasal shelf portion and includes (i) a first support wall extending from the lower oral support portion and being made of a first material having a first durometer, and (ii) a second support wall extending from the upper nasal support portion and being made of a second material having a second durometer that is higher than the first durometer.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
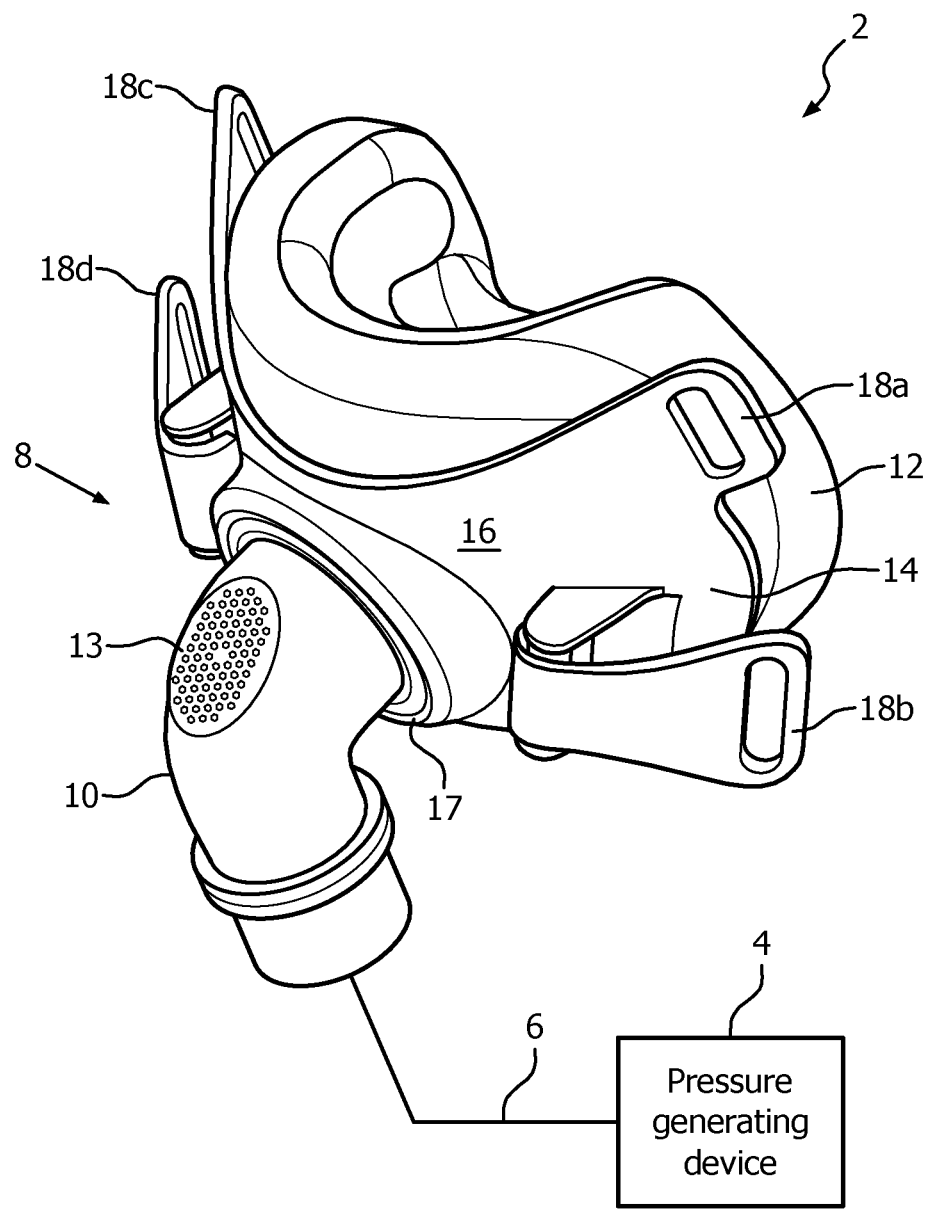
FIGS. 1 and 2 are schematic diagrams (including isometric and front views, respectively) of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, a "substantially fluid tight seal" means that two surfaces sealingly engage each other in a manner that substantially limits passage of a fluid between the two surfaces (e.g., no more than 5% passage). As used herein, the term "sealingly" or "sealed" in the context of an engagement, attachment or coupling means that two parts are coupled to one another with a substantially fluid tight seal.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
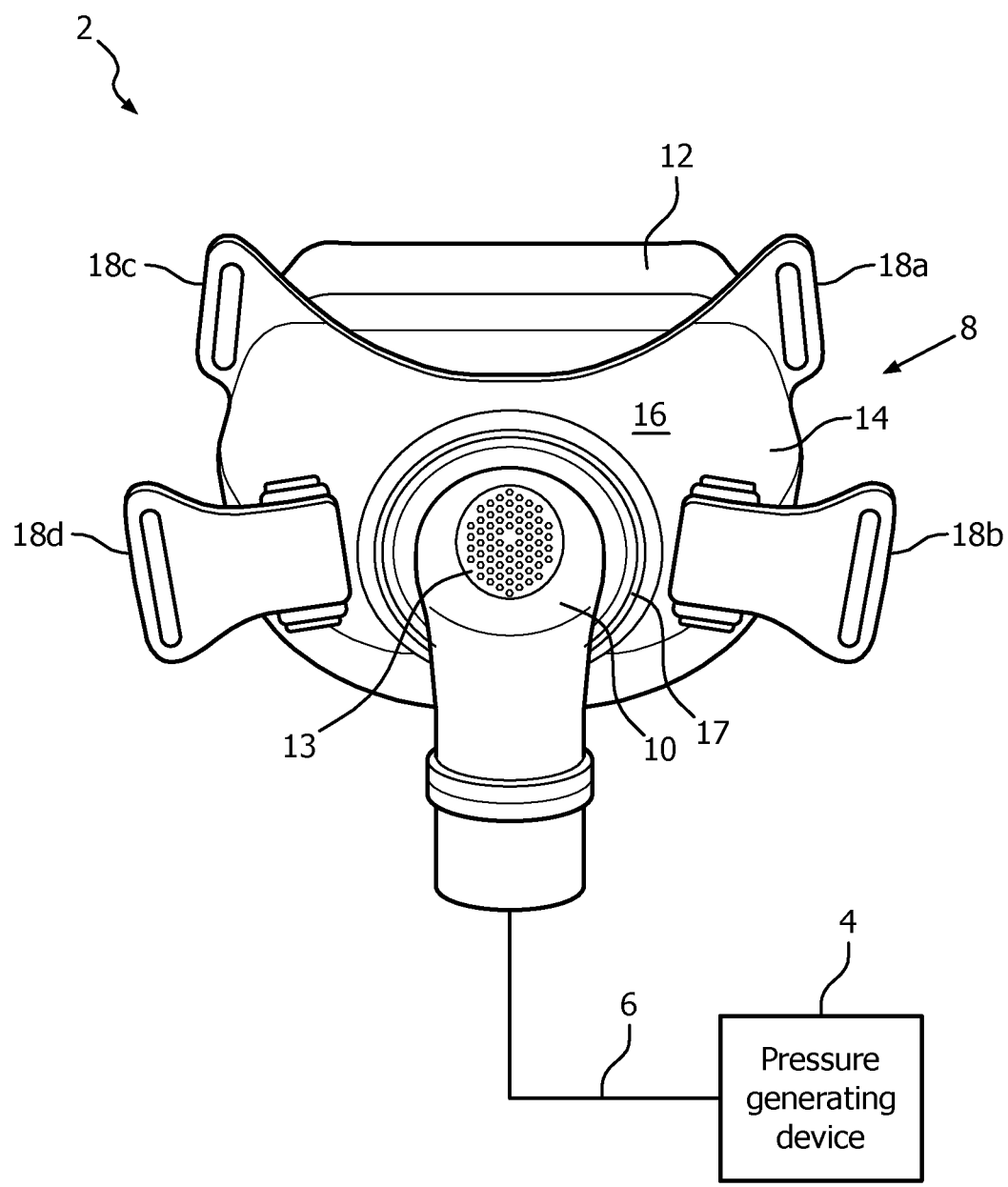

A system 2 adapted to provide a regimen of respiratory therapy to a patient according to one exemplary embodiment of the invention is generally shown in FIGS. 1 and 2. System 2 includes a pressure generating device 4, a delivery conduit 6, and a patient interface device 8 including an elbow conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the illustrated, non-limiting embodiment (described in detail herein), patient interface device 8 comprises an inflatable subnasal sealing cushion that is structured to deliver breathing gas to the airway of the patient through both the patient's mouth and through the patient's nose. It will be appreciated, however, that the illustrated embodiment is meant to be exemplary only and that other, alterative subnasal sealing cushion embodiments are contemplated within the scope of the present invention. In the embodiment shown in FIG. 1, patient interface device 8 includes a cushion assembly 12 and a frame member 14 having a faceplate portion 16. Cushion assembly 12 is coupled to a rear side of frame member 14.

Frame member 14 is made of a rigid or semi-rigid material, such as, without limitation, an injection molded thermoplastic or silicone. Straps (not shown) of a headgear component may be attached to faceplate portion 16 via attachment members 18a, 18b, 18c and 18d to secure patient interface device 8 to the patient's head. As seen in FIGS. 1 and 2, attachment members 18a and 18c are fixedly attached to faceplate portion 16, and attachment members 18b and 18d are pivotably attached to faceplate portion 16. An opening 17 in faceplate portion 16 to which elbow conduit 10 is coupled allows the flow of breathing gas from pressure generating device 4 to be communicated to an interior space defined by cushion assembly 12, and then, to the airway of a patient. Opening 17 in faceplate portion 16 also allows the flow of exhalation gas (from the airway of such a patient) to be communicated to exhaust vent 13 provided in elbow conduit 10.

Figure 3:
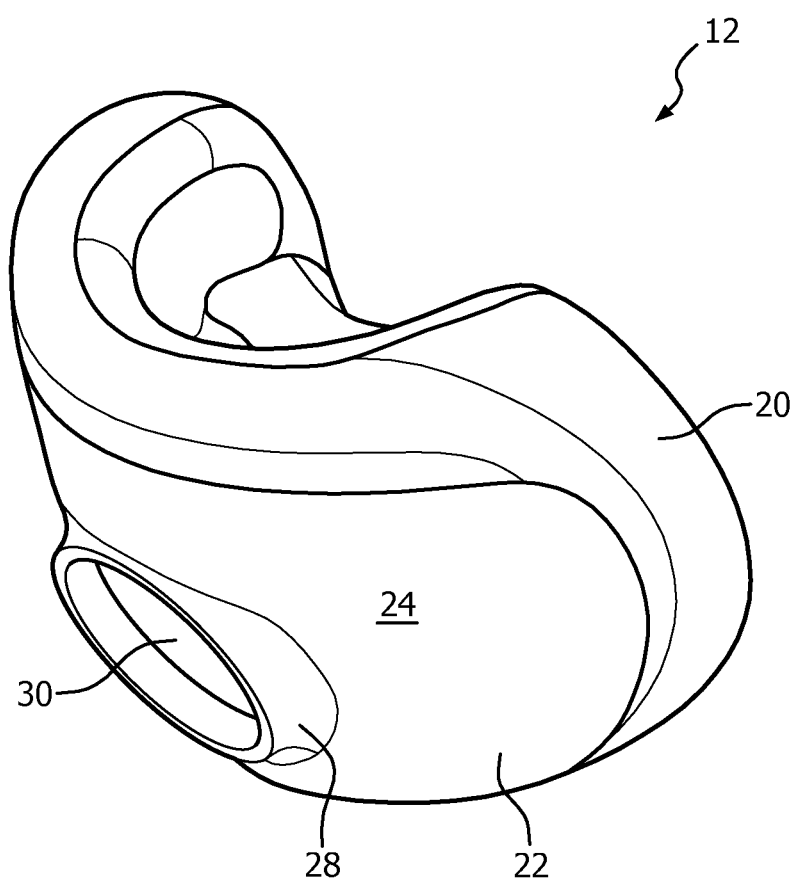
FIG. 3 is a front isometric view of a cushion assembly forming part of a patient interface device of the system of FIGS. 1 and 2 according to one non-limiting exemplary embodiment of the present in invention.

FIG. 3 is a front isometric view of cushion assembly 12 according to one non-limiting exemplary embodiment of the present in invention. Cushion assembly 12 includes a cushion member 20 coupled to a support frame 22, each of which is described in detail herein.

Figure 4:
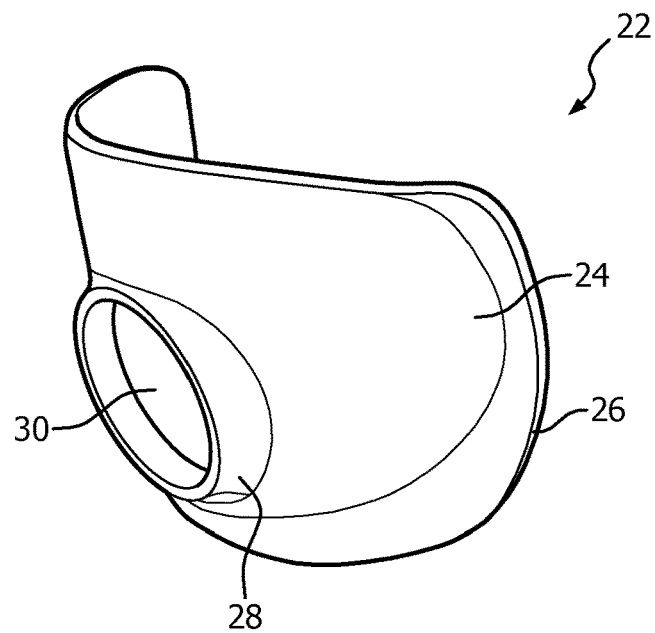
FIG. 4 is a front isometric view and FIG. 5 is a rear isometric view of a support frame forming part of the cushion assembly of FIG. 3.
Figure 5:
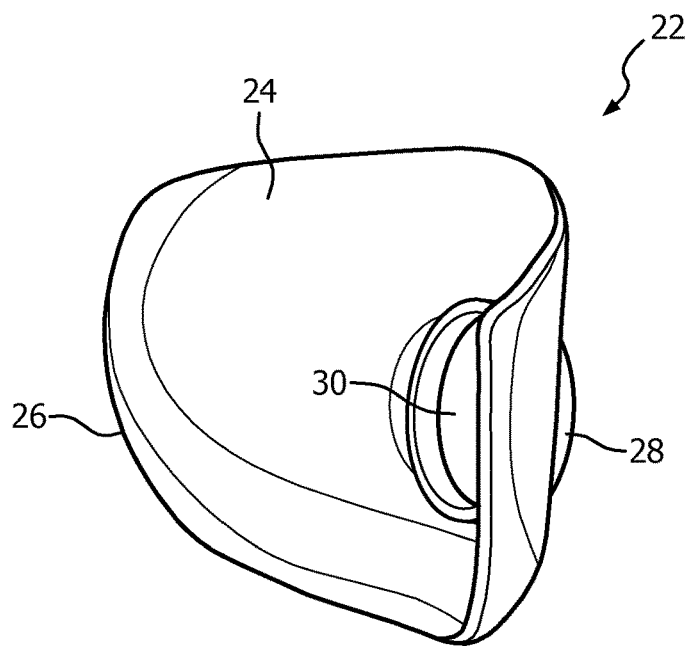

FIG. 4 is a front isometric view and FIG. 5 is a rear isometric view of support frame 22 according to the present exemplary embodiment. Support frame 22 is made from a rigid or semi-rigid material, such as, without limitation, an injection molded thermoplastic or silicone, and facilitates secure connection of cushion assembly 12 to frame member 14 and elbow conduit 10. Support frame 22 includes an arc-shaped main body portion 24 having an outer edge 26 defining an outer perimeter thereof, and a short cylindrical port member 28 extending from main body portion 24. Port member 28 defines an opening 30. As seen in FIGS. 1 and 2, when patient interface device 8 is assembled, elbow conduit 10 extends through the opening in faceplate portion 16 and is coupled to port member 28 to enable elbow conduit 10 to be fluidly coupled to cushion assembly 12 through opening 30.

Figure 6:
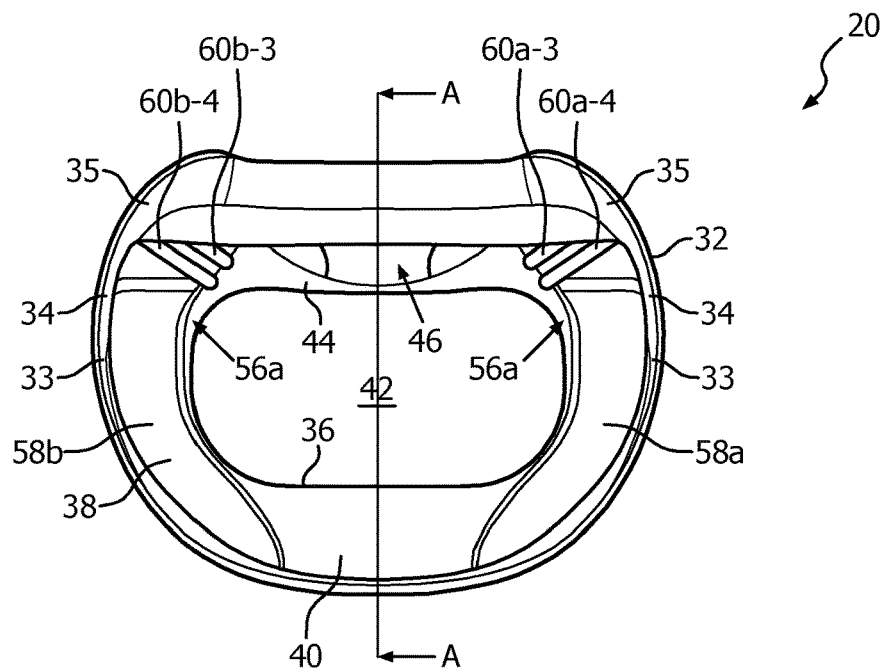
FIGS. 6, 7, 8 and 9 are front elevational, rear elevational, top plan and side elevational views, respectively, of a cushion member forming part of the cushion assembly of FIG. 3.
Figure 7:
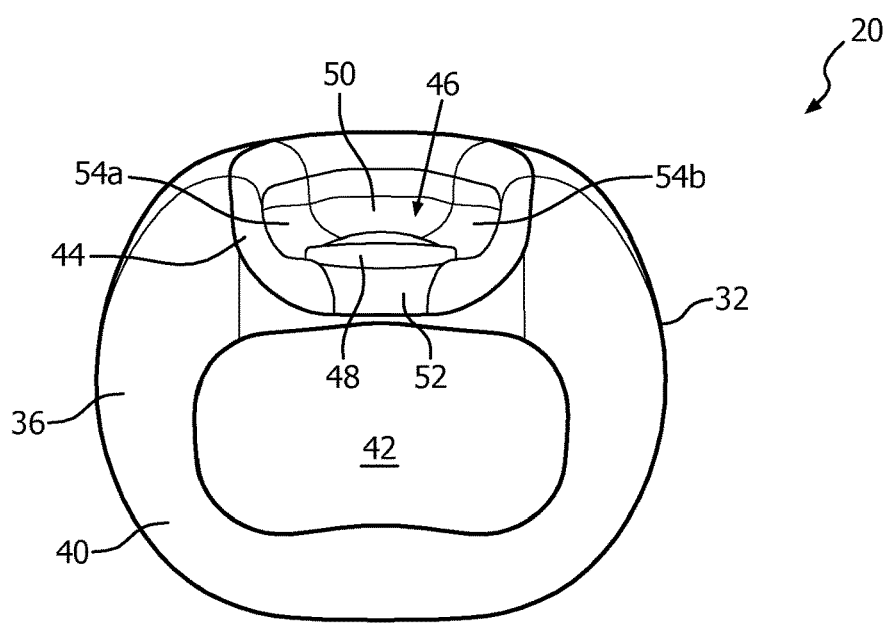
Figure 8:
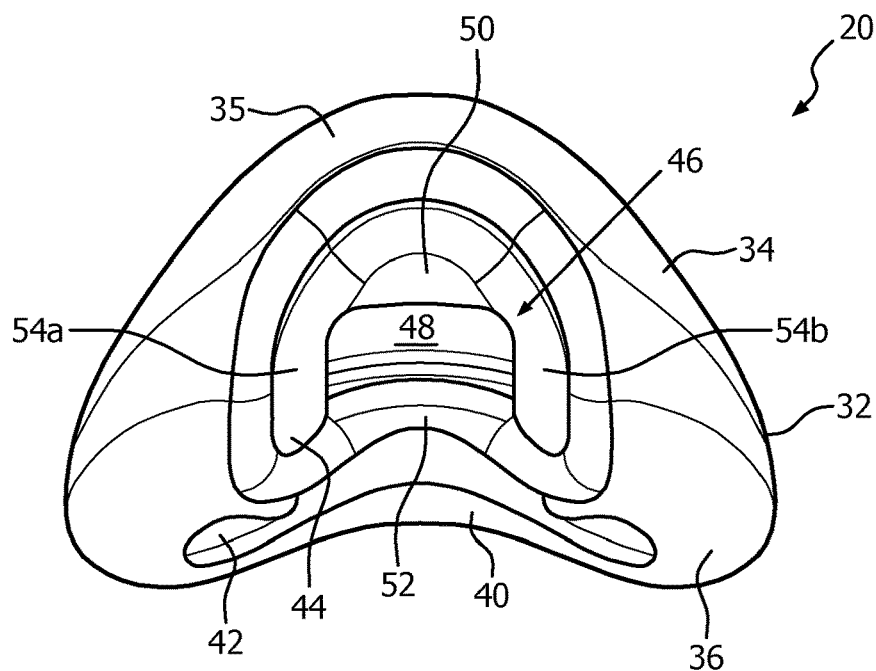
Figure 9:
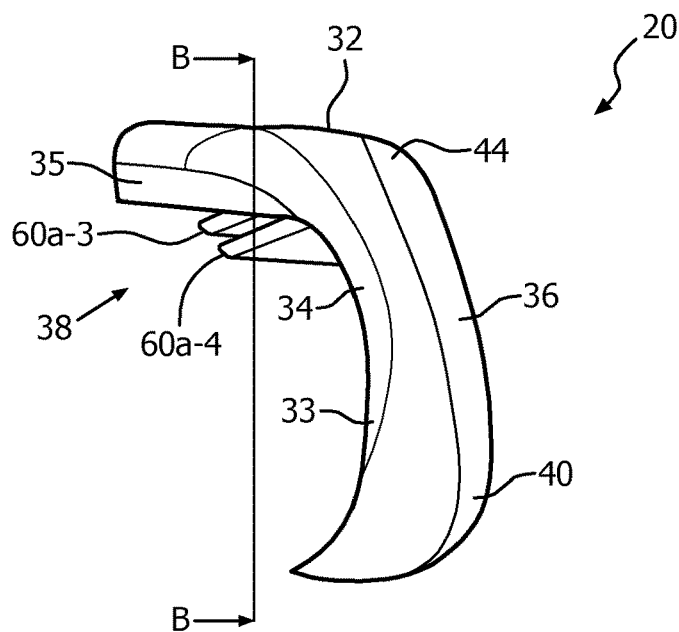
Figure 10:
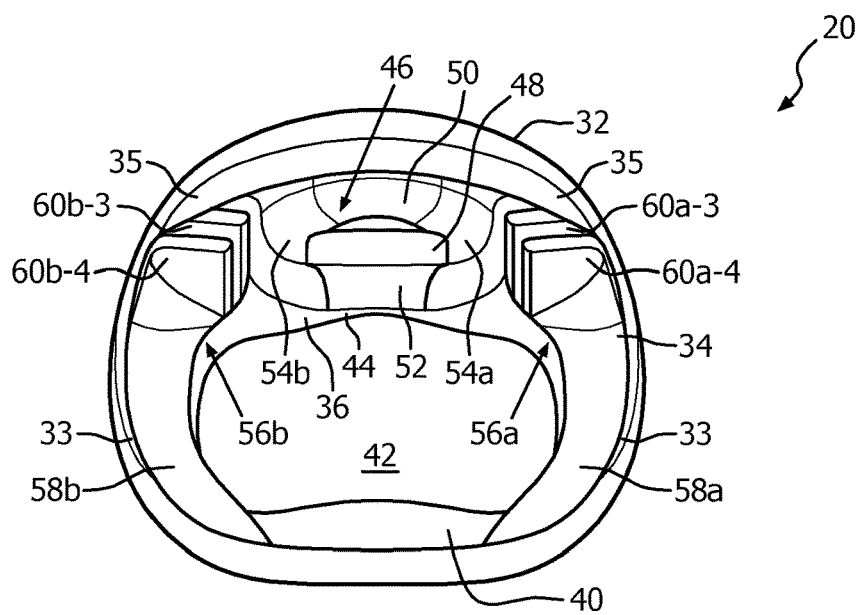
FIGS. 10 and 11 are front and side isometric views, respectively, of the cushion member of FIGS. 6-9.
Figure 11:
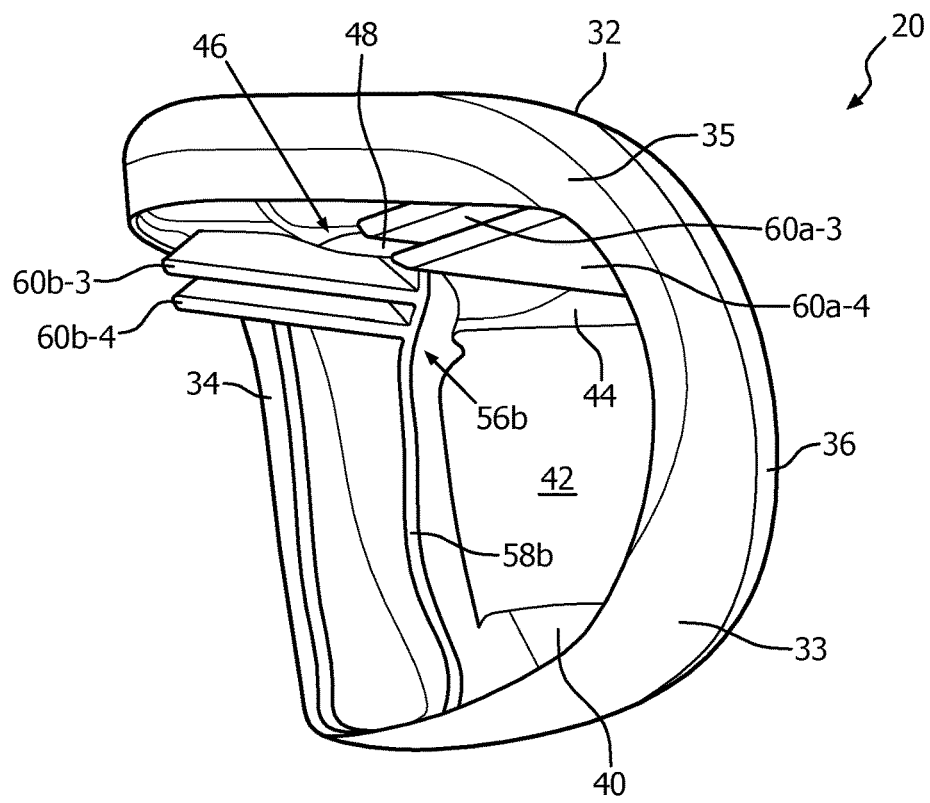
Figure 12:
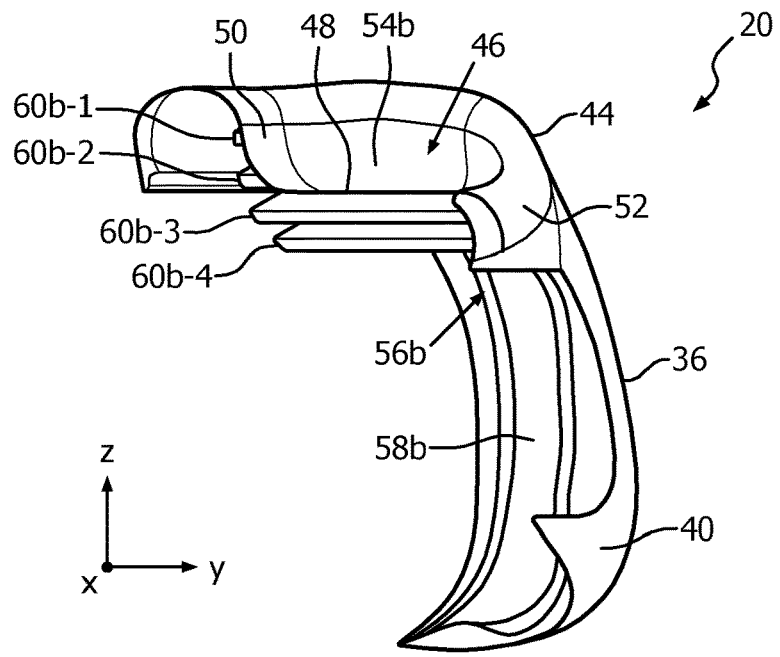
FIG. 12 is a cross-sectional view of the cushion member taken along lines A-A of FIG. 6.
Figure 13:
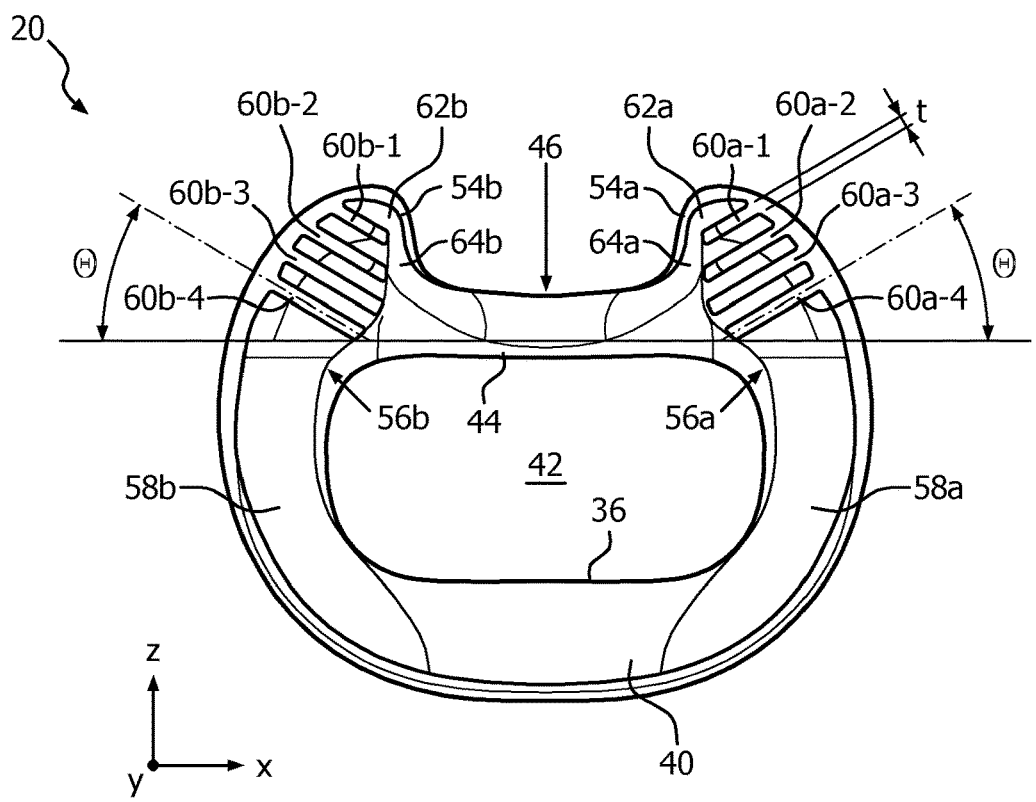
FIG. 13 is a cross-sectional view of the cushion member taken along lines B-B of FIG. 9.

FIGS. 6, 7, 8 and 9 are front elevational, rear elevational, top plan and side elevational views, respectively, of cushion member 20 according to one exemplary embodiment of the present invention. In addition, FIGS. 10 and 11 are front and side isometric views, respectively, of cushion member 20, FIG. 12 is a cross-sectional view of cushion member 20 taken along lines A-A of FIG. 6, and FIG. 13 is a cross-sectional view of cushion member 20 taken along lines B-B of FIG. 9.

In the exemplary embodiment, cushion member 20 is defined from a unitary piece of soft, flexible, cushiony, elastomeric material, such as, without limitation, silicone or an appropriately soft thermoplastic elastomer, or any combination of such materials. It will be understood, however, that cushion member 20 does not need to be unitary within the scope of the present invention. Rather, cushion member 20, and the parts thereof (described herein), may be made of separate components that are coupled to one another by suitable means.

Cushion member 20 includes an inflatable main body portion 32 that has a support portion 34 located on a first (front) side of main body portion 32 and a sealing flap portion 36 coupled to support portion 34 and defining a rear side of main body portion 32. Support portion 34 includes a front orifice 38 that is sized and shaped to mate with main body portion 24 of support frame 22 to enable a substantially fluid tight seal to be created between support frame 22 and cushion member 20. In addition, support portion 34 can be divided into a lower oral support portion 33 and an upper nasal support portion 35, each of which is described in more detail elsewhere herein.

Sealing flap portion 36 includes an oral sealing portion 40 (lower part of sealing flap portion 36) that transitions into a nasal sealing portion 44 (upper part of sealing flap portion 36). Oral sealing portion 40 includes an oral orifice 42, and is structured to contact the user's face and surround the user's lips (such that oral orifice 42 receives the user's mouth) when patient interface device 8 is donned by the user. Nasal sealing portion 44 includes a nasal shelf portion 46 which defines a nasal orifice 48 that is substantially provided in a nasal orifice plane. Nasal shelf portion 46 is structured to contact the bottom of the user's nose (i.e. the bottoms of the alare, which is the region defining the openings of the nostrils of the user) to create a seal therewith when patient interface device 8 is donned by the user.

Nasal shelf portion 46 thus includes a top region 50, a bottom region 52 and opposite side regions 54a, 54b which together define nasal orifice 48 and which are structured to contact the bottom of the user's nose. In the exemplary embodiment, to accommodate the user's anatomy, top region 50 and side regions 54a, 54b form walls and extend in an upward (first) direction away from the nasal orifice plane, and bottom region 52 extends in a downward (second/opposite) direction away from the nasal orifice plane. When nasal shelf portion 46 is contacted by the bottom of the patient's as just described, the nasal cavity of the user will be in fluid communication with the inside of cushion member 20 through nasal orifice 48.

Sealing flap portion 36 has a relatively thin cross-sectional thickness (e.g., ≤0.01 to 0.02 inches), which makes it highly flexible. As a result, sealing flap portion 36, and in particular nasal shelf portion 46, will tend to easily deform and collapse in response to a force being applied thereto by the patient's face (e.g., the patient's nose). In order to counteract such a tendency for deformation and collapse, cushion member 20 is in accordance with the present invention provided with a support structure which provides support for the sealing flap portion 36, and in particular nasal shelf portion 46.

In the exemplary embodiment shown in FIGS. 6-13, the support structure is in the form of first and second ribbed structures 56a, 56b provided on opposite sides (the left and right sides) of support portion 34. More specifically, ribbed structure 56a is provided on a first (left when viewed from the rear) side of support portion 34 and includes: (i) an elongated rib 58a extending from the outer wall of lower oral support portion 33, and (ii) a number of ribs 60a extending (linearly in the illustrated embodiment) from the outer wall of upper nasal support portion 35 underneath nasal shelf portion 46 (specifically, underneath side region 54a). In the illustrated embodiment, ribs 60a are also coupled to and extend from elongated rib 58a and run generally perpendicular to the plane in which the orifice 30 is provided (and thus generally perpendicular to the face of the patient).

In an alternative embodiment, ribs 60a may be separate and spaced from elongated rib 58a. Similarly, ribbed structure 56b is provided on a second (right when viewed from the rear) side of support portion 34 and includes: (i) an elongated rib 58b extending from the outer wall of lower oral support portion 33, and (ii) a number of ribs 60b extending (linearly in the illustrated embodiment) from the outer wall of upper nasal support portion 35 underneath nasal shelf portion 46 (specifically, underneath side region 54b). In the illustrated embodiment, ribs 60b are also coupled to and extend from elongated rib 58b and run generally perpendicular to the plane in which the orifice 30 is provided (and thus generally perpendicular to the face of the patient). In an alternative embodiment, ribs 60b may be separate and spaced from elongated rib 58b.

In the exemplary embodiment, as best seen in FIG. 13, ribbed structure 56a includes four ribs 60a (labeled 60a-1, 60a-2, 60a-3, 60a-4) and ribbed structure 56b includes four ribs 60b (labeled 60b-1, 60b-2, 60b-3, 60b-4). It will be understood, however, that four ribs 60a and four ribs 60b as just described is meant to be exemplary only and that more or less ribs 60a, 60b are also contemplated within the scope of the present invention. Also in the exemplary embodiment (see FIG. 13), a gap or space 62a is provided in between the top of rib 60a-1 (the first or upper-most rib) and the bottom of side region 54a, and a gap or space 62b is provided in between the top rib 60b-1 (the first or upper-most rib) and the bottom of side region 54*b*. The gaps 62*a* and 62*b* allow for flexible inflation. Moreover, a gap or space 64*a* is provided in between the outer distal edges of ribs 60*a* and the bottom of side region 54*a*, and a gap or space 64*b* is provided in between the outer distal edges of ribs 60*b* and the bottom of side region 54*b* (see FIG. 13). The gaps 64*a* and 64*b* provide clearance for wider noses (i.e., limited alare interference).

In addition, in the exemplary embodiment, as best seen in FIG. 13, each of the ribs 60*a* and 60*b* is disposed at an angle θ with respect to a plane that is parallel to the nasal orifice plane (described above). In various alternative embodiments, θ may be specified as follows: (i) 0°≤θ≤90°, (ii) 30°≤θ≤60°, (iii) 0°≤θ≤60°, (iv) 0°≤θ≤45°, or (v) 0=45°. Furthermore, in the exemplary embodiment, the cross-sectional thickness (t) of each rib 60*a* and 60*b* is ≥1.0 mm (or, alternatively, 1.5 mm or 2 mm), and the durometer of the material forming each rib 60*a* and 60*b* is 30 shore A to 60 shore A (in one particular embodiment, the durometer is about 40 shore A (±5%)).

Thus, the angled rib design located on the left (aligned ribs 60*a*) and right (aligned ribs 60*b*) sides of the alare as just described provides adequate support to nasal shelf portion 46 in the y-direction (FIG. 13), which is the direction that collapse is most likely. The ribs 60*a* and 60*b* also place necessary pressure on the tissue by the alare base to seal the very difficult crease. The geometry and angle of the ribs 60*a* and 60*b* maintains and enhances the versatility of the inflated seal, allowing a multitude of nasal widths and depths to utilize one cushion size. Thus, the ribs 60*a* and 60*b* are able to deflect for wider nose geometries while still providing the necessary x and y direction forces to prevent collapse and provide seal support. Also, when an outside pressure, for example by a pillow, is provided generally in the x-direction during therapy, the ribs 60*a* and 60*b* are able to deflect in the z-direction (which deflection is facilitated by the angled nature in certain embodiments) when a counteractive force is applied by the alare in the x-direction. This deflection prevents cushion member 20 from closing off/collapsing the nares.

Figure 14:
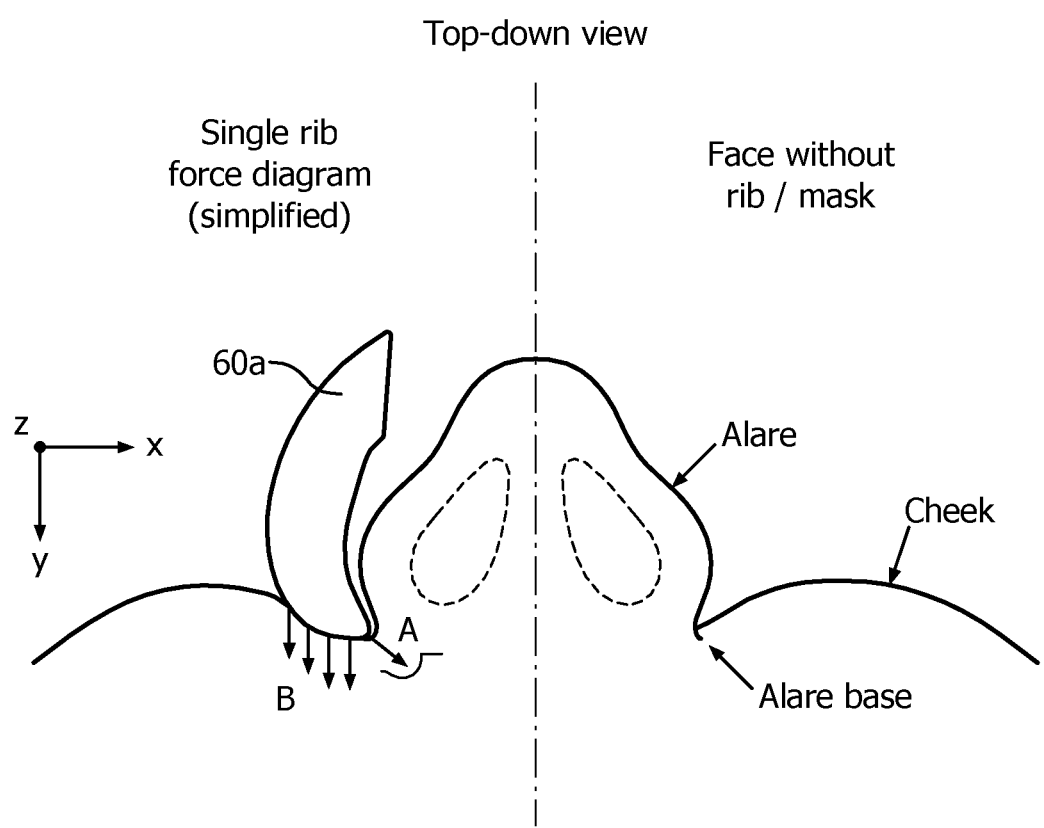
FIG. 14 is a schematic diagram illustrating the forces provided by the cushion member of FIGS. 6-9.

Moreover, the benefits of the angled rib design just described are further illustrated with reference to FIG. 14, which schematically shows the angled rib design in simplified form (with one rib 60*a*) adjacent to a view of the face without a cushion. As seen in FIG. 14, the rib geometry provides a point force indicated by the arrow A which seals off the alare base crease/nook by slightly displacing tissue. In addition, as indicated by the arrows labeled B, the rib(s) 60*a*, 60*b* distribute the mounting force in the x direction and, where multiple ribs 60 are used (e.g., FIGS. 1-13), the force is also distributed in the z direction. This creates solid platform for inflation of sealing flap portion 36, and in particular nasal shelf portion 46, around the nose and prevents collapse of nasal shelf portion 46. In addition, as seen in FIG. 14, a slight tissue displacement occurs at the alare base to ensure a robust seal.

Furthermore, as noted above, in the illustrated embodiment, ribs 60*a* are coupled to and extend from the upper part of elongated rib 58*a*, and ribs 60*b* are coupled to and extend from the upper part of elongated rib 58*a*. As a result, ribs 60*a* are connected together by a sheet (the upper part of elongated rib 58*a*) of elastomeric material, such as silicone, provided on the x-z plane, and ribs 60*b* are connected together by a sheet (the upper part of elongated rib 58*b*) of elastomeric material, such as silicone, provided on the x-z plane. Tying the ribs 60*a* and 60*b* together in this manner provides more structure/support ability and makes cushion member 20 more comfortable by providing an additional flat surface between the ends of the ribs and the patient's face.

Figure 15:
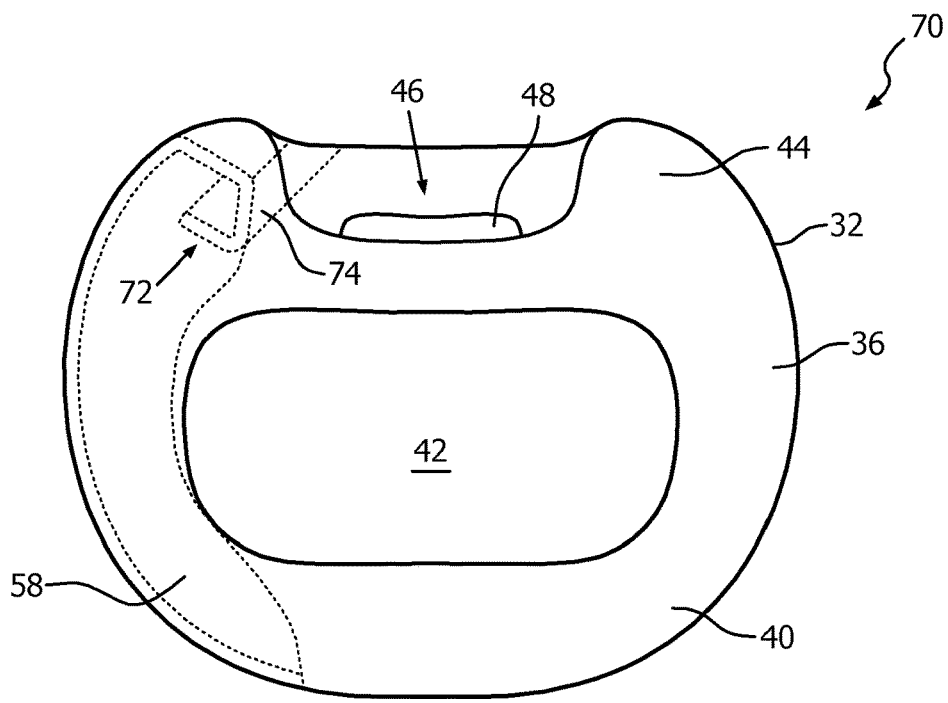
FIGS. 15-23 are front views of a number of alternative cushion members that may form part of the cushion assembly of FIG. 3.

FIG. 15 is a front view of an alternative cushion member 70 according to an alternative exemplary embodiment. Cushion member 70 is similar to (and may be substituted for) cushion member 20, and like components are labeled with like reference numerals. Cushion member 70, however, includes an alternative support structure 72 (shown in phantom lines) provided on each side of cushion member 70 which provides support for the sealing flap portion 36, and in particular nasal shelf portion 46. As seen in FIG. 15, support structure 72 includes a rib member 74 extending from the outer wall underneath nasal shelf portion 46 and having a C-shaped cross-section having a first leg extending from the outer wall, a second leg transverse to the first leg, and a third leg transverse to the second leg. Rib member 74 runs generally perpendicular to the plane in which the orifice 30 is provided (and thus generally perpendicular to the face of the patient).

Figure 16:
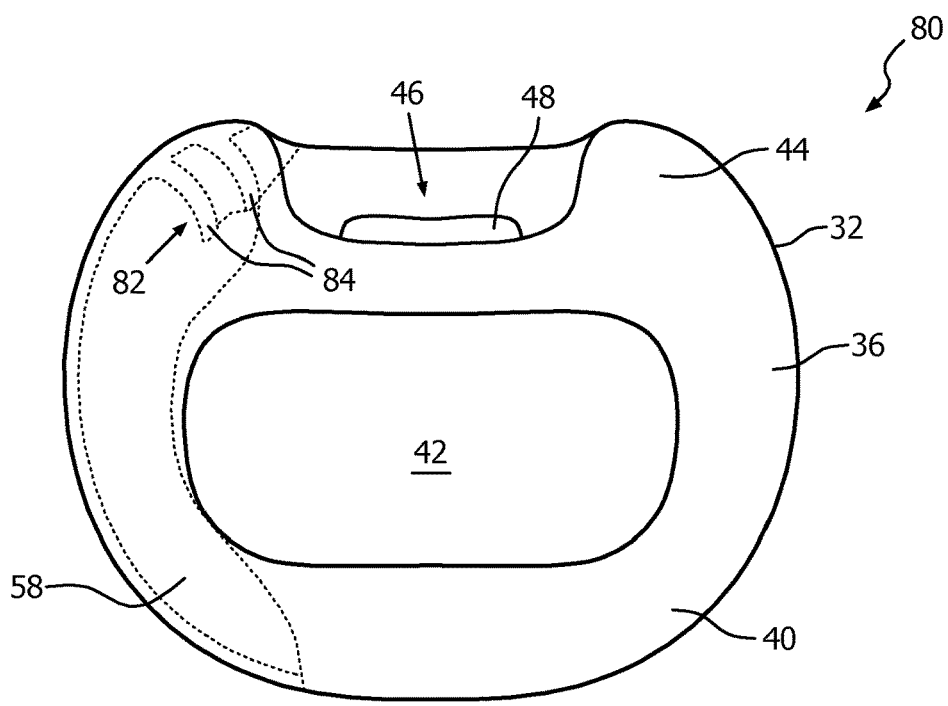

FIG. 16 is a front view of another alternative cushion member 80 according to an alternative exemplary embodiment. Cushion member 80 is similar to (and may be substituted for) cushion member 20, and like components are labeled with like reference numerals. Cushion member 80, however, includes an alternative support structure 82 (shown in phantom lines) provided on each side of cushion member 80 which provides support for the sealing flap portion 36, and in particular nasal shelf portion 46. As seen in FIG. 16, support structure 82 includes a plurality of arced shaped ribs 84 extending from the outer wall underneath nasal shelf portion 46. Ribs 84 run generally perpendicular to the plane in which the orifice 30 is provided (and thus generally perpendicular to the face of the patient).

Figure 17:
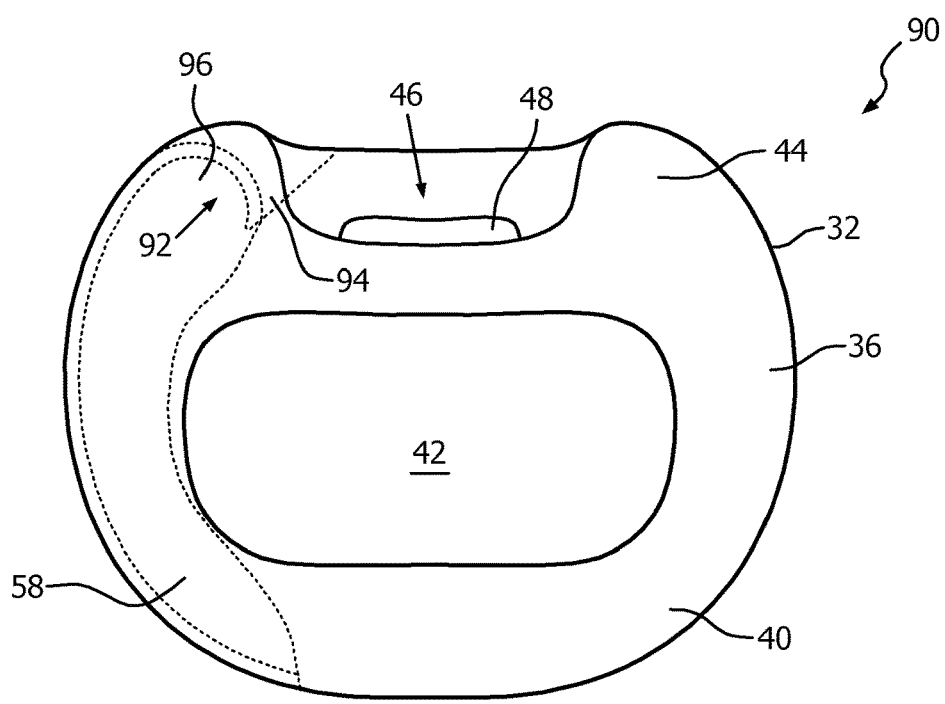

FIG. 17 is a front view of another alternative cushion member 90 according to an alternative exemplary embodiment. Cushion member 90 is similar to (and may be substituted for) cushion member 20, and like components are labeled with like reference numerals. Cushion member 90, however, includes an alternative support structure 92 (shown in phantom lines) provided on each side of cushion member 90 which provides support for the sealing flap portion 36, and in particular nasal shelf portion 46. As seen in FIG. 17, support structure 92 includes a single curved rib 94 extending from the outer wall underneath nasal shelf portion 46 in a hook-like fashion and having a curved cross-section which defines an inner pocket 96. Rib 94 runs generally perpendicular to the plane in which the orifice 30 is provided (and thus generally perpendicular to the face of the patient). The amount of curvature on rib 94 can vary to suit the particular needs of a particular application. It is noted that the single curved rib 94 helps to simplify manufacturing (specifically molding the silicone part) and cleaning.

Figure 18:
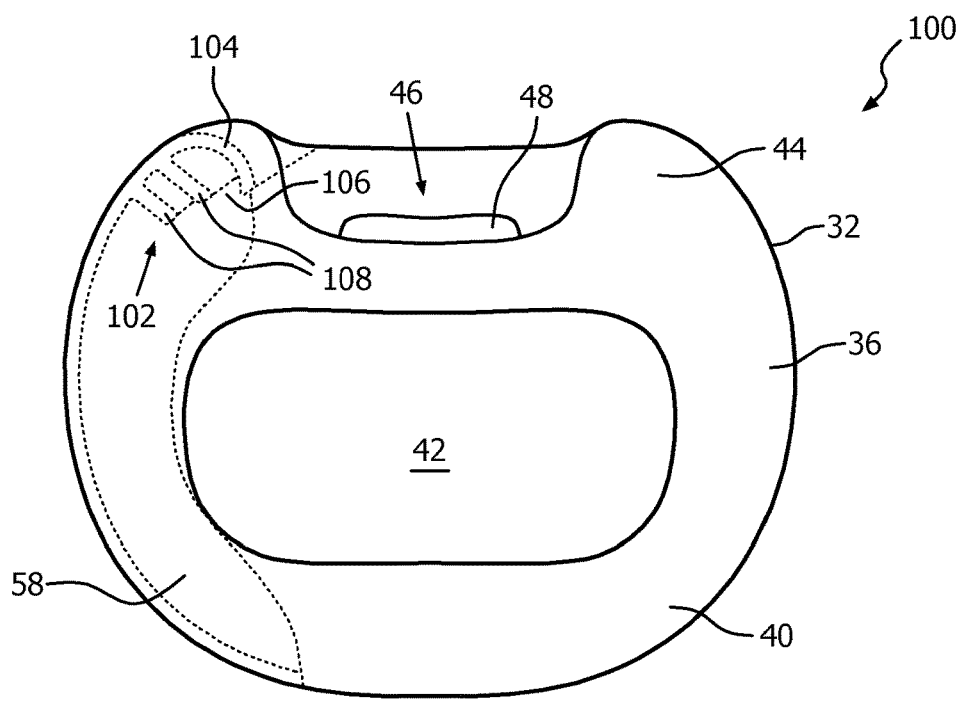

FIG. 18 is a front view of another alternative cushion member 100 according to an alternative exemplary embodiment. Cushion member 100 is similar to (and may be substituted for) cushion member 20, and like components are labeled with like reference numerals. Cushion member 100, however, includes an alternative support structure 102 (shown in phantom lines) provided on each side of cushion member 100 which provides support for the sealing flap portion 36, and in particular nasal shelf portion 46. As seen in FIG. 18, support structure 102 includes a single curved rib 104 extending from the outer wall underneath nasal shelf portion 46 in a hook-like fashion and having a curved cross-section which defines an inner pocket 106, and one or more linear rib members 108 extending from the outer wall and within the pocket 106 underneath the rib 104. Rib 94 and rib members 108 run generally perpendicular to the plane in which the orifice 30 is provided (and thus generally perpendicular to the face of the patient).

Figure 19:
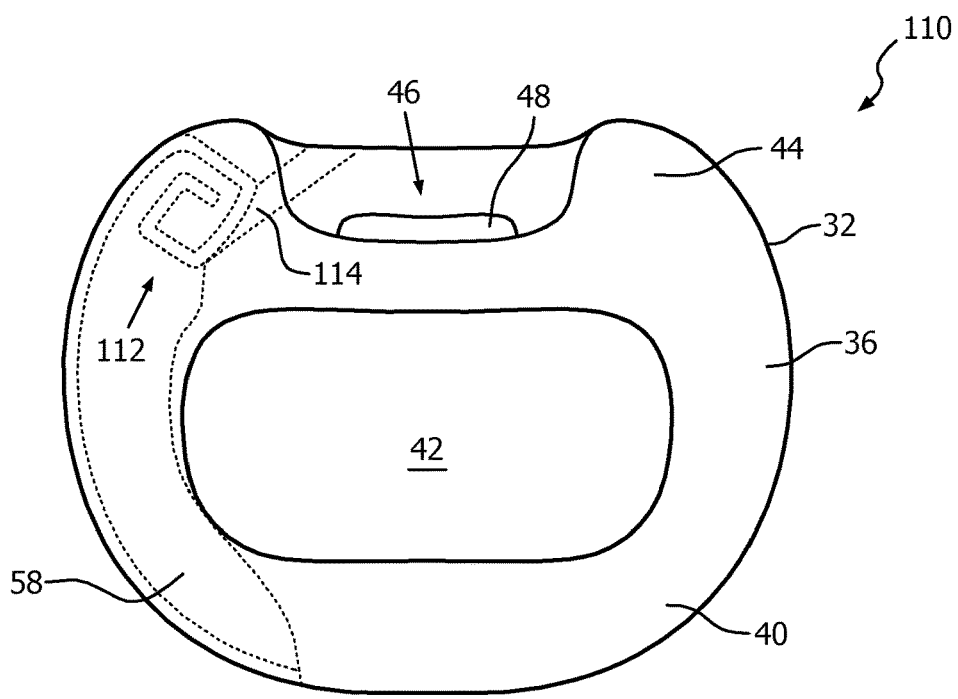

FIG. 19 is a front view of an alternative cushion member 110 according to another alternative exemplary embodiment. Cushion member 110 is similar to (and may be substituted for) cushion member 20, and like components are labeled with like reference numerals. Cushion member 110, however, includes an alternative support structure 112 (shown in phantom lines) provided on each side of cushion member 110 which provides support for the sealing flap portion 36, and in particular nasal shelf portion 46. As seen in FIG. 19, support structure 112 includes a rib member 114 extending from the outer wall underneath nasal shelf portion 46 and having a spiral-shaped cross-section. Rib member 114 runs generally perpendicular to the plane in which the orifice 30 is provided (and thus generally perpendicular to the face of the patient).

Figure 20:
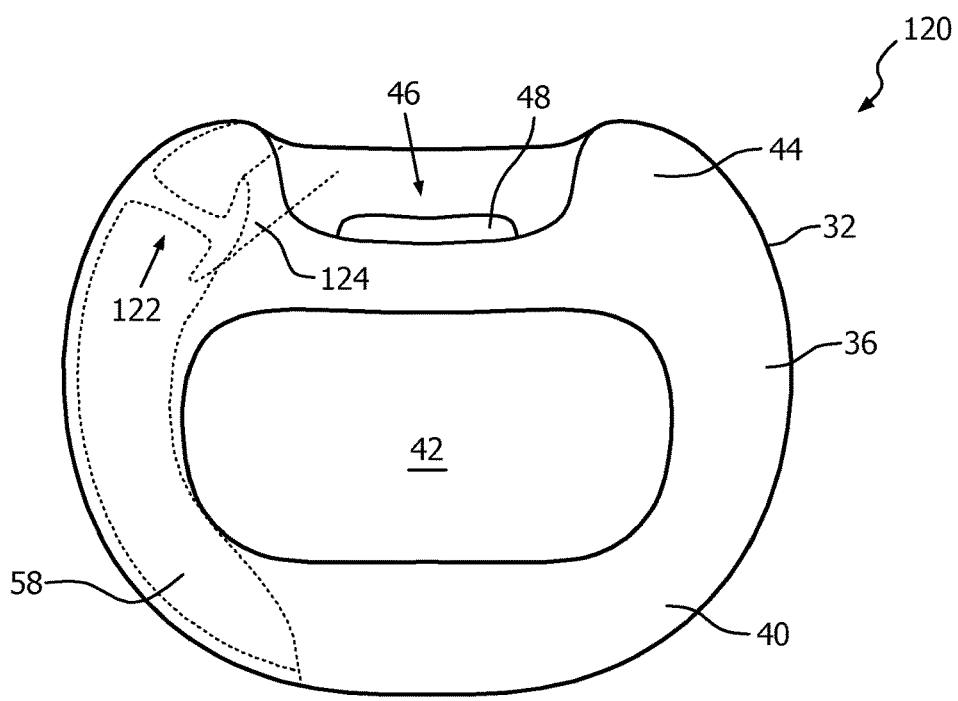

FIG. 20 is a front view of an alternative cushion member 120 according to another alternative exemplary embodiment. Cushion member 120 is similar to (and may be substituted for) cushion member 20, and like components are labeled with like reference numerals. Cushion member 120, however, includes an alternative support structure 122 (shown in phantom lines) provided on each side of cushion member 120 which provides support for the sealing flap portion 36, and in particular nasal shelf portion 46. As seen in FIG. 20, support structure 122 includes a rib member 124 extending from the outer wall underneath nasal shelf portion 46 and having a T-shaped cross-section. Rib member 124 runs generally perpendicular to the plane in which the orifice 30 is provided (and thus generally perpendicular to the face of the patient). The T-shaped cross-section of rib member 124 allows for pivoting around the y axis and can allow movement as the patient opens his or her mouth (to relieve potential maxilla pressure) or as a larger nose is placed on nasal shelf portion 46.

Figure 21:
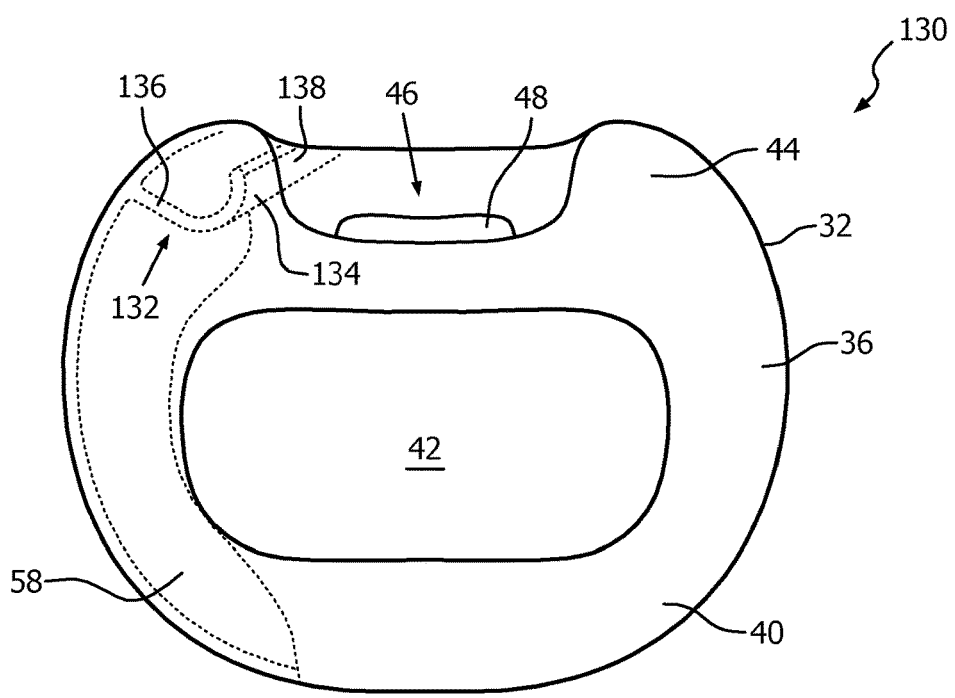

FIG. 21 is a front view of an alternative cushion member 130 according to another alternative exemplary embodiment that employs a specific rib design for allowing for nose width flexibility while simplifying the design. Cushion member 130 is similar to (and may be substituted for) cushion member 20, and like components are labeled with like reference numerals. Cushion member 130, however, includes an alternative support structure 132 (shown in phantom lines) provided on each side of cushion member 130 which provides support for the sealing flap portion 36, and in particular nasal shelf portion 46. As seen in FIG. 21, support structure 132 includes a rib member 134 extending from the outer wall underneath nasal shelf portion 46 and having a first leg 136 extending from the outer wall and a second leg 138 transverse to first leg 136 that extends from an end of first leg 136 toward nasal shelf portion 46. Rib member 134 runs generally perpendicular to the plane in which the orifice 30 is provided (and thus generally perpendicular to the face of the patient).

Figure 22:
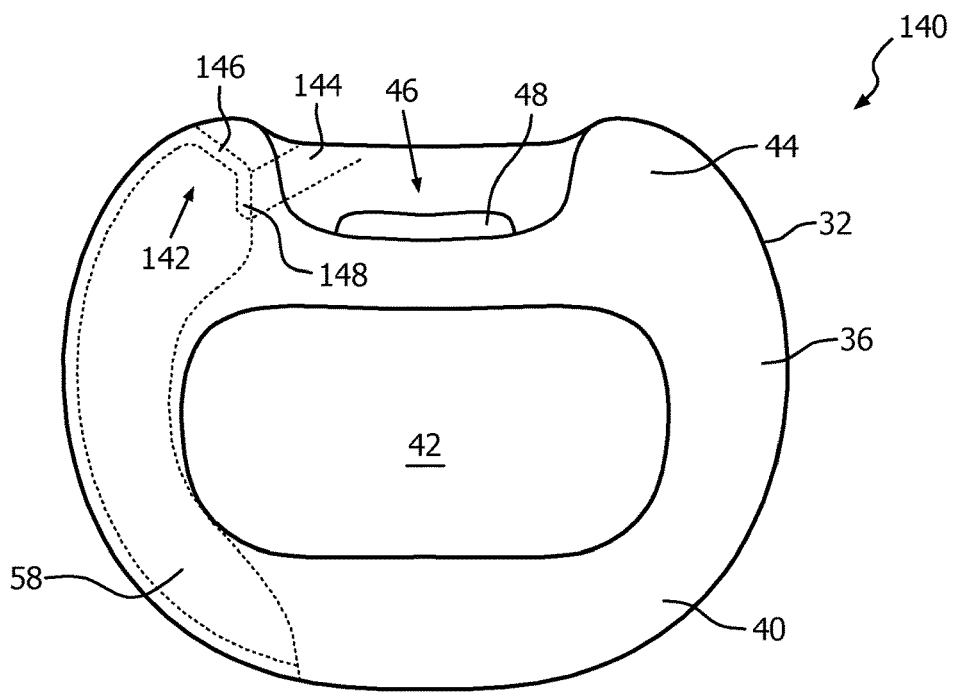

FIG. 22 is a front view of an alternative cushion member 140 according to another alternative exemplary embodiment that employs a specific rib design that provides for ease of manufacturing. Cushion member 140 is similar to (and may be substituted for) cushion member 20, and like components are labeled with like reference numerals. Cushion member 140, however, includes an alternative support structure 142 (shown in phantom lines) provided on each side of cushion member 140 which provides support for the sealing flap portion 36, and in particular nasal shelf portion 46. As seen in FIG. 22, support structure 142 includes a rib member 144 extending from the outer wall underneath nasal shelf portion 46 and having a first leg 146 extending from the outer wall and a second leg 148 transverse to first leg 146 that extends from an end of first leg 146 away from nasal shelf portion 46. Rib member 144 runs generally perpendicular to the plane in which the orifice 30 is provided (and thus generally perpendicular to the face of the patient).

Figure 23:
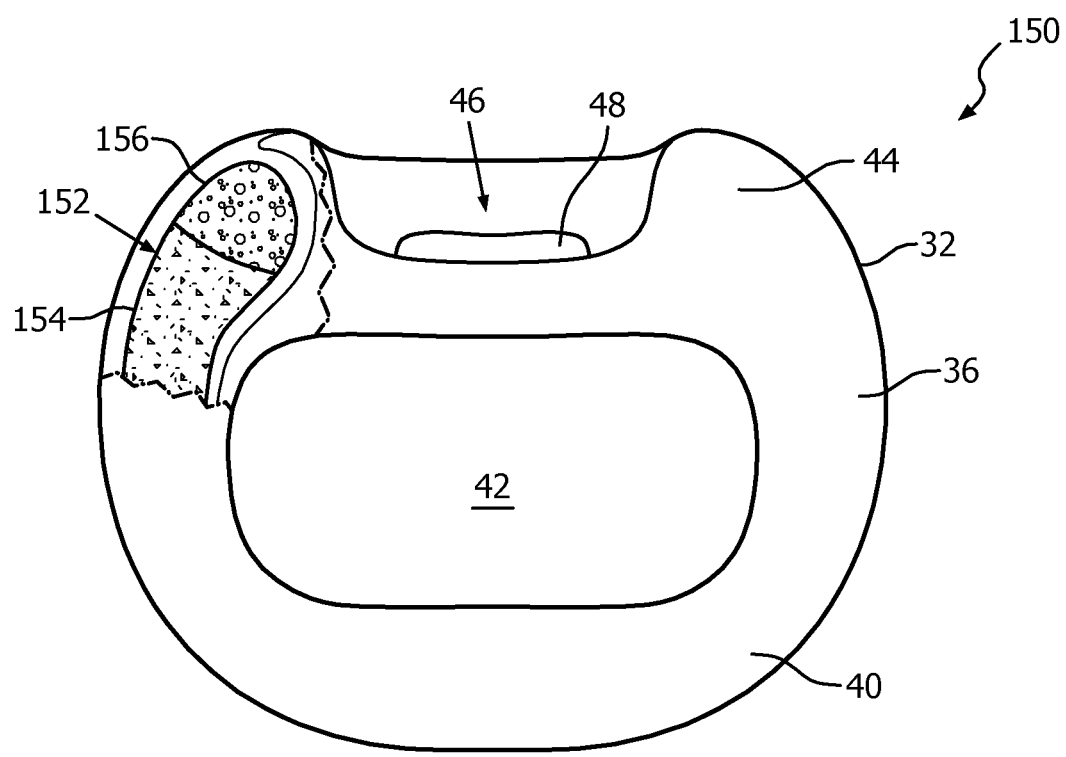

FIG. 23 is a front view (in partial cut away) of an alternative cushion member 150 according to another alternative exemplary embodiment. Cushion member 150 is similar to (and may be substituted for) cushion member 20, and like components are labeled with like reference numerals. Cushion member 150, however, includes an alternative support structure 152 (shown through the cut away portion) provided on each side of cushion member 150 which provides support for the sealing flap portion 36, and in particular nasal shelf portion 46. As seen in FIG. 22, support structure 142 is positioned under and spaced from a bottom of nasal shelf portion 46 and includes (i) a first support wall 154 extending from the lower oral support portion and being made of a first material having a first durometer (e.g., 5 shore 00 to 10 shore 00), and (ii) a second support wall 156 extending from the upper nasal support portion and being made of a second material having a second durometer that is higher than the first durometer (e.g., 15 shore 00 to 30 shore 00). The first and/or second materials may be a viscoelastic material, such as a gel substance comprising a viscoelastic polyurethane polymer, or an elastic material. As used herein, the term viscoelastic material shall mean a material that exhibits both viscous and elastic characteristics when undergoing deformation, and as a result exhibits time dependent strain. A viscoelastic material will thus deform under the influence of an applied stress, and when the stress is removed from the material, the material will slowly and not instantaneously recover from at least a portion of the deformation. As used herein, the term elastic material shall mean a material that exhibits elastic but not viscous characteristics when undergoing deformation. Elastic materials deform under the influence of an applied stress and return instantaneously to their original state once the stress is removed, thereby recovering from all of the deformation.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A subnasal sealing cushion for a patient interface device structured to deliver a flow of breathing gas to an airway of a user, comprising:
  a cushion member having a front side and a rear side opposite the front side, the rear side being structured to face a face of the user responsive to the patient interface device being donned by the user, the cushion member including:
    a support portion having an outer wall and a support structure coupled to the outer wall and extending longitudinally along a first direction, the first direction extending from the front side to the rear side, and
    a sealing flap portion coupled to the support portion, the sealing flap portion including a nasal shelf portion, the nasal shelf portion defining a nasal orifice and being structured to contact a bottom of a nose of the user to create a seal therewith responsive to the patient interface device being donned by the user,
  wherein the support structure is positioned under and spaced a predetermined distance from a bottom surface of the nasal shelf portion,
  wherein the nasal shelf portion includes opposite side regions which together define the nasal orifice and which are structured to contact the bottom of the user's nose,
  wherein the support structure is positioned proximate the side regions in order to provide support to the nasal shelf portion and prevent collapse thereof, and
  wherein the support structure comprises a first plurality of ribs and a second plurality of ribs, each of the first and second pluralities of ribs being coupled to and extending from the outer wall, each of the first plurality of ribs being spaced from one another and positioned one on top of the other, and each of the second plurality of ribs being spaced from one another and positioned one on top of the other.

2. The subnasal sealing cushion according to claim 1, wherein the nasal orifice is substantially provided in a nasal orifice plane, wherein each of the ribs is disposed linearly at an angle $\theta$ with respect to a plane that is parallel to the nasal orifice plane, wherein $0° \leq \theta \leq 90°$.

3. The subnasal sealing cushion according to claim 2, wherein $30° \leq \theta \leq 60°$.

4. The subnasal sealing cushion according to claim 3, wherein $\theta = 45°$.

5. The subnasal sealing cushion according to claim 3, wherein a cross-sectional thickness (t) of each rib is $\geq 1.0$ mm.

6. The subnasal sealing cushion according to claim 5, wherein a cross-sectional thickness (t) of the nasal shelf portion is $\leq 0.02$ inches.

7. The subnasal sealing cushion according to claim 1, wherein the support portion including the outer wall and the support structure and the nasal shelf portion are made of a first material, the first material being an elastomeric material; wherein the subnasal sealing cushion is a single unitary piece of material; and wherein the support portion and the sealing flap portion are portions of the single unitary piece of material.

8. The subnasal sealing cushion according to claim 1, wherein the support portion includes a lower oral support portion and an upper nasal support portion, wherein the support structure is coupled to the upper nasal support portion, wherein the sealing flap portion includes an oral sealing portion that transitions into a nasal sealing portion that includes the nasal shelf portion, wherein the oral sealing portion includes an oral orifice that is structured to receive a mouth of the user responsive to the patient interface device being donned by the user.

9. The subnasal sealing cushion according to claim 8, further comprising a support frame, wherein the cushion member has a front orifice located opposite the oral orifice, and wherein the cushion member is mated with the support frame at the front orifice in a manner wherein a substantially fluid tight seal is created between the support frame and the cushion member.

10. The subnasal sealing cushion according to claim 8, wherein the lower oral support portion includes an elongated support rib extending from an outer wall of the lower oral support portion.

11. The subnasal sealing cushion according to claim 10, wherein a longitudinal end of the support structure is attached to the elongated support rib.

12. The subnasal sealing cushion according to claim 1, wherein at least one of the first plurality of ribs and the second plurality of ribs extends in a hook-like fashion and has a curved cross-section which defines an inner pocket.

13. The subnasal sealing cushion according to claim 12, further comprising one or more linear rib members extending from the outer wall and within the pocket underneath the at least one of the first plurality of ribs and the second plurality of ribs.

14. A subnasal sealing cushion for a patient interface device structured to deliver a flow of breathing gas to an airway of a user, comprising:
  a cushion member having a front side and a rear side opposite the front side, the rear side being structured to face a face of the user responsive to the patient interface device being donned by the user, the cushion member including:
    a support portion having a lower oral support portion, an upper nasal support portion, a support structure coupled to an outer wall of the support portion and extending longitudinally along a first direction, the first direction extending from the front side to the rear side, and
    a sealing flap portion coupled to the support portion, the sealing flap portion including an oral sealing portion that transitions into a nasal shelf portion, the nasal shelf portion defining a nasal orifice and being structured to contact a bottom of a nose of the user to create a seal therewith responsive to the patient interface device being donned by the user, the oral sealing portion having an oral orifice that is structured to receive a mouth of the user responsive to the patient interface device being donned by the user,
  wherein the support structure is positioned under and spaced a predetermined distance from a bottom surface of the nasal shelf portion,
  wherein the nasal shelf portion includes opposite side regions which together define the nasal orifice and which are structured to contact the bottom of the user's nose,
  wherein the support structure is positioned proximate the side regions in order to provide support to the nasal shelf portion and prevent collapse thereof,
  wherein the support structure includes a first support wall extending from the lower oral support portion and being made of a first material having a first durometer, and a second support wall extending from the upper nasal support portion and being made of a second material having a second durometer that is higher than the first durometer, and wherein the support structure comprises a first plurality of ribs and a second plurality of ribs, each of the first and second pluralities of ribs being coupled to and extending from the outer wall, each of the first plurality of ribs being spaced from one another and positioned one on top of the other, and each of the second plurality of ribs being spaced from one another and positioned one on top of the other.

15. The subnasal sealing cushion according to claim 14, wherein the first durometer is 5 shore 00 to 10 shore 00 and the second durometer is 15 shore 00 to 30 shore 00.

16. The subnasal sealing cushion according to claim 15, wherein the first material is a first gel material and the second material is a second gel material.

\* \* \* \* \*